(12) United States Patent
Naitou et al.

(10) Patent No.: US 8,390,913 B2
(45) Date of Patent: Mar. 5, 2013

(54) CIRCULARLY POLARIZED LIGHT-EMITTING NANOPARTICLE

(75) Inventors: Masanobu Naitou, Nara (JP); Kenji Iwahori, Nara (JP)

(73) Assignee: National University Corporation Nara Institute of Science and Technology, Nara (JP)

(*) Notice: Subject to any disclaimer, the term of this patent is extended or adjusted under 35 U.S.C. 154(b) by 166 days.

(21) Appl. No.: 12/935,066

(22) PCT Filed: Mar. 26, 2009

(86) PCT No.: PCT/JP2009/056060
§ 371 (c)(1),
(2), (4) Date: Sep. 28, 2010

(87) PCT Pub. No.: WO2009/122994
PCT Pub. Date: Oct. 8, 2009

(65) Prior Publication Data
US 2011/0038025 A1     Feb. 17, 2011

(30) Foreign Application Priority Data
Mar. 29, 2008   (JP) .................. 2008-088945

(51) Int. Cl.
G02F 1/03      (2006.01)
G02F 1/00      (2006.01)
G02B 26/08     (2006.01)
(52) U.S. Cl. ............... 359/241; 359/301; 359/321
(58) Field of Classification Search ............ 359/241, 359/237–238, 247, 265–270, 290–291, 301, 359/303–304, 321
See application file for complete search history.

(56) References Cited

U.S. PATENT DOCUMENTS

| | | | |
|---|---|---|---|
| 6,121,075 A | 9/2000 | Yamashita | |
| 6,287,928 B1 | 9/2001 | Yamashita | |
| 6,319,738 B1 | 11/2001 | Yamashita | |
| 6,635,494 B2 | 10/2003 | Yamashita | |
| 6,660,379 B1 | 12/2003 | Lakowicz et al. | |
| 7,015,139 B2 | 3/2006 | Yamashita | |
| 7,796,242 B2 | 9/2010 | Hasegawa et al. | |
| 2007/0141163 A1* | 6/2007 | Vitaliano et al. | 424/490 |
| 2009/0233377 A1 | 9/2009 | Iwahori | |

FOREIGN PATENT DOCUMENTS

JP    2003086715 A    3/2003

OTHER PUBLICATIONS

Satrijo et al., "Probing a Conjugated Polymer's Transfer of Organization-Dependent Properties from Solutions to Films" (Abstract), J. Am. Chem. Soc., 2006, 128 (28), pp. 9030-9031, Jun. 22, 2006.

(Continued)

*Primary Examiner* — Dawayne A Pinkney
(74) *Attorney, Agent, or Firm* — Ogilvie Law Firm

(57) ABSTRACT

Provided is a compound semiconductor nanoparticle that exhibits circularly polarized luminescence characteristics. CdS prepared inside a core of ferritin, which is a cage-like protein, exhibits a high circularly polarized luminescence (CPL). A wavelength of the circularly polarized luminescence (CPL) can be controlled by laser irradiation, thereby enabling utilization of the compound semiconductor nanoparticle in the field of bionanotechnology, for example, in creating a WORM (Write-Once Read-Many times) memory. As the cage-like protein, which is a protein with a cavity formed therein, a protein belonging to the ferritin protein family, such as apoferritin, or a recombinant thereof can be used.

12 Claims, 17 Drawing Sheets

(a)

(b)

OTHER PUBLICATIONS

Moloney et al. "Chiral highly luminescent CdS quantum dots", Chem. Commun., 2007, pp. 3900-3902, Oct. 14, 2007.

Kenji Iwahori et al: "Cadmium Sulfide Nanoparticle Synthesis in Dps Protein from Listeria innocua", Chemistry of Materials, vol. 19, No. 13, pp. 3105-3111, Jun. 1, 2007.

Kenji Iwahori et al: "Bio-template Synthesis of Nanoparticle by Cage-shaped Protein Supramolecule, Apoferritin", Journal of Cluster Science, Kluwer Academic Publishers—Plenum Publishers, NE, vol. 18, No. 2, pp. 358-370, May 26, 2007.

* cited by examiner (a) Thiourea    (b) Thioacetic

Apoferritin
(Without a core
made up of CdS)

Apoferritin
(a core made
up of CdS)

(a) Thiourea (b) Thioacetic

Apoferritin
(Without a core
made up of ZnS)

Apoferritin
(a core made
up of ZnS)

CIRCULARLY POLARIZED LIGHT-EMITTING NANOPARTICLE

RELATED APPLICATIONS

This application claims priority to PCT/JP2009/056060 filed 26 Mar. 2009, and to JP 2008-088945 filed 29 Mar. 2008, which are incorporated herein.

TECHNICAL FIELD

The present invention relates to a microparticle that exhibits a property of emitting circularly polarized light and particularly relates to a circularly polarized light-emitting nanoparticle made up of a compound semiconductor nanoparticle encapsulated in ferritin (apoferritin).

BACKGROUND ART

Recently in the field of biotechnology, remarkable developments are being made, applications to other fields are being sought, and research on application to semiconductor microfabrication technology (bionanotechnology) is also being pursued. In the biotechnology field, products (amino acid residues) can be controlled at the molecular level based on a blueprint called "DNA," and all proteins formed from the various amino acid residues have a self-assembling ability that enables forming of "nanoblocks" that are not dispersed in size. Thus by employing biotechnology, the formation of a product can be controlled at the nanoscale, and in the incorporation of a semiconductor component in the product, application of biotechnology to semiconductor microfabrication technology becomes apparent.

Here, as arts in which biotechnology is applied to semiconductor microfabrication technology, arts of forming a quantum dot using a cage-like protein called ferritin, which is present in living bodies, have been disclosed (refer to Patent Document 1 and Patent Document 2).

As shown in FIG. 1, ferritin has a structure that includes a spherical protein outer shell portion, which has a diameter of 12 nm and is made up of 24 protein monomer, and a core portion 1A, which is a central portion of the outer shell portion, has a diameter of approximately 6 nm, absorbs Fe ions from inside a living body, and holds the ions in the form of an oxide. Ferritin is called a cage-like protein due to having the protein outer shell portion and the core portion. Ferritin has an active site that oxidizes the absorbed Fe ions, and the Fe ions are accumulated as the oxide, $5Fe_2O_3 \cdot 9H_2O$.

A protein with which the metal oxide core is removed from the ferritin is called apoferritin, and besides Fe, apoferritin is capable of accumulating microparticles made of various metals, such as nickel (Ni), cobalt (Co), manganese (Mn), etc. TEM images of various metal nanoparticles prepared inside apoferritin are shown in FIG. 2

As described above, ferritin has the structure including the metal oxide in the core portion and the outer shell in which 24 protein monomers are assembled together. The ferritin has a self-assembling ability and can thus be formed readily as a uniform film, and the outer shell proteins have a characteristic of being readily decomposed and removed by UV ozone heat treatment, etc.

Here, the self-assembling ability of ferritin can be utilized to control an adsorption position of ferritin on a semiconductor substrate, and by selectively removing the outer shell protein of the ferritin, a structure with which the core metal oxide is aligned in a two-dimensional matrix as shown in FIG. 2 can be prepared.

It is also known that, with ferritin, a nanoparticle of a compound semiconductor, formed of two or more types of elements, can be prepared in the core portion (refer to Patent Document 3).

Due to a quantum confinement effect, a nanoparticle of a compound semiconductor expresses physical properties that differ greatly from those of a bulk state. In particular, such nanoparticles have ideal fluorescence characteristics, such as a high luminance, a high light resistance, a broad excitation spectrum, and a narrow fluorescence spectrum, and are thus attracting attention as next-generation optoelectronic materials. Meanwhile, since the development of a water-soluble compound semiconductor nanoparticle that uses a hydrophilic coating molecule, active research is being carried out on applications of compound semiconductor nanoparticles to biotechnology, such as bioimaging, immunoassay, etc.

By the art disclosed in Patent Document 3, use of a quantum size effect of a microparticle made of a semiconductor has become possible, and in a case of a compound semiconductor microparticle that emits fluorescence when excited, use in a biological substance labeling method, etc., has become possible. TEM images of various compound semiconductor nanoparticles prepared inside apoferritin are shown in FIG. 3.

As described above, compound semiconductor nanoparticles are gathering attention as a next-generation optoelectronic material. However presently, the circumstances are such that the uses of compound semiconductor nanoparticles in the biotechnology field are limited to alternatives to light-emitting organic molecules. Up to now, the present inventors, with an aim at creating highly luminescent circularly polarized light-emitting molecules, have created helical polymers, aromatic low-molecular-weight molecules, and compound semiconductor nanoparticles that are optically active and light-emitting and have examined circularly polarized luminescence (CPL) characteristics of these substances.

Circularly polarized luminescence (CPL) refers to a difference in emission intensities of right circularly polarized light and left circularly polarized light emitted from an optically active molecule (see FIG. 4). Although such circularly polarized luminescence (CPL) has been used from before for evaluation of a steric structure of an organic molecule in an excited state, application to polarized light sources for high-luminance liquid crystal displays as well as three-dimensional displays, memory materials, optical communication, and other forms of advanced light information processing are being anticipated recently.

As substances exhibiting circularly polarized luminescence (CPL), bioluminescent substances, light-emitting rare earths, optically active conjugate polymers, etc., are known. Among compound semiconductors, GaAs has been reported to exhibit circularly polarized luminescence when excited by a circularly polarized laser. However, there have been no reports so far of circularly polarized luminescence being achieved with a compound semiconductor nanoparticle (see, for example, Non-Patent Document 1). Although as an attempt to see if a compound semiconductor exhibits circularly polarized luminescence (CPL) has been made in regard to circular dichroism (CD) active CdS synthesized from an optically active thiol compound, this report indicated that the compound semiconductor nanoparticle is CPL inactive (see Non-Patent Document 2).

PRIOR ART DOCUMENTS

[Patent Document 1] JP99-45990A
[Patent Document 2] JP2003-086715A
[Patent Document 2] WO2007/032241

[Non-Patent Document 1] J. Am. Chem. Soc., 128, 9030 (2006).

[Non-Patent Document 2] Chem. Commun., M. P. Moloney, et al., 2007, page 3900.

DISCLOSURE OF THE INVENTION

Problems to be Solved by the Invention

As described above, compound semiconductor nanoparticles are gathering attention as a next-generation optoelectronic material. However presently, the circumstances are such that the uses of compound semiconductor nanoparticles in the biotechnology field are limited to alternatives to light-emitting organic molecules. Also with the conventional arts, it has not been possible to prepare a compound semiconductor nanoparticle that exhibits circularly polarized luminescence characteristics.

An object of the present invention is to provide, in view of the above, a compound semiconductor nanoparticle that exhibits circularly polarized luminescence characteristics.

Means to Solve the Objects

As a result of diligent research, the present inventors found that a compound semiconductor nanoparticle that exhibits circularly polarized luminescence can be synthesized by performing synthesis of a compound semiconductor inside a protein and have thereby come to complete the present invention.

Specifically, it was found that CdS prepared inside a core of ferritin, which is a cage-like protein, exhibits a strong circularly polarized luminescence (CPL). This is the first example of circularly polarized luminescence (CPL) from a compound semiconductor nanoparticle. Also, as shall be described below, a wavelength of the circularly polarized luminescence (CPL) can be adjusted by laser irradiation, and as an application of a compound semiconductor nanoparticle in the biotechnology field, application to creation of a WORM (Write-Once Read-Many times) memory, etc., is thereby enabled.

In order to achieve the above object, a first aspect of the present invention provides a circularly polarized light-emitting nanoparticle made up of a compound semiconductor nanoparticle encapsulated in a cage-like protein.

As the cage-like protein, which is a protein having a cavity formed therein, a protein belonging to the ferritin protein family, such as apoferritin, or a recombinant thereof can be used.

Here, apoferritin is preferably selected for the protein nanoparticle. Apoferritin has such merits as enabling alignment at a high density due to having a self-aligning ability, the ferritin protein being extremely low in shape and size variations, enabling a low manufacturing cost due to being simple in preparation process, etc. In a case where apoferritin is used, an internal space thereof has a diameter of no more than approximately 7 nm and a compound semiconductor nanoparticle of a nanometer order can thus be prepared efficiently. Also preferably, a II-VI compound semiconductor is selected as the compound semiconductor. Especially preferably, CdS or ZnS is selected.

Next, a second aspect of the present invention provides a circularly polarized light-emitting nanoparticle made up of a compound semiconductor nanoparticle that is surface-modified by a protein.

With the circularly polarized light-emitting nanoparticle according to the first aspect, the cage-like protein is not only used as an optically active protective agent but also as a reaction site for microparticle formation. As a hypothesis, it is considered that circularly polarized luminescence is exhibited by an effect of a chiral field inside the ferritin.

Meanwhile, the circularly polarized light-emitting nanoparticle according to the second aspect of the present invention is made up of the compound semiconductor nanoparticle that is surface-modified by a protein.

That is, even in a case where a protein chemically modifies a surface of the compound semiconductor nanoparticle, the compound semiconductor nanoparticle exhibits circularly polarized luminescence by the effect of the chiral field in the same manner as the compound semiconductor nanoparticle encapsulated inside ferritin.

Here preferably, the compound semiconductor is a II-VI compound semiconductor or a III-V compound semiconductor. The range of compound semiconductors that can be used can thus be widened and usability is improved in comparison to the circularly polarized light-emitting nanoparticle according to the first aspect of the present invention.

Next, a third aspect of the present invention provides a wavelength control method for circularly polarized light-emitting nanoparticle, with which a circularly polarized luminescence wavelength can be controlled by laser irradiation of the circularly polarized light-emitting nanoparticle. That is, with the wavelength control method according to the present invention, the circularly polarized luminescence wavelength is made adjustable by application of an external stimulus, such as laser irradiation, etc., to the circularly polarized light-emitting nanoparticle.

As a present hypothesis, it is assumed that laser irradiation of the ferritin microparticle encapsulating the compound semiconductor nanoparticle (circularly polarized light-emitting nanoparticle) causes the compound semiconductor nanoparticle inside the ferritin to undergo a photooxidation reaction and thereby causes a shift to longer wavelength. That is, as a cause of occurrence of the shift to longer wavelength, it was observed that, due to preferential photooxidation of a direct transition (crystalline) portion, significant light emission occurs from a trap level (longer wavelength) at an interface. By using the wavelength control method for circularly polarized light-emitting nanoparticle, the circularly polarized luminescence wavelength of the circularly polarized light-emitting nanoparticle can be shifted to a longer wavelength.

It is also possible to shift a fluorescence wavelength to a shorter wavelength by laser irradiation of the circularly polarized light-emitting nanoparticle. By the laser irradiation, the nanoparticle is decreased in diameter size and the emission wavelength of the trap level is accordingly shifted to shorter wavelength. In this case, fluorescence emission due to direct transition is hardly observed.

Also, by using the wavelength control method for circularly polarized light-emitting nanoparticle, it becomes possible to form a quantum dot memory made up of the circularly polarized light-emitting nanoparticles.

Specifically, a fluorescence spectrum obtained by measuring a ferritin microparticle encapsulating the compound semiconductor CdS with a normal spectrofluorometer exhibits an emission peak near 700 nm, which is considered to be due to the trap level as shown in FIG. 5, and a circularly polarized luminescence spectrum obtained by circularly polarized luminescence (CPL) measurement exhibits a circularly polarized luminescence peak near 500 nm as shown in FIG. 6. However, after laser irradiation is performed on the ferritin microparticle encapsulating the compound semiconductor CdS, the emission wavelength in fluorescence measurement by the spectrofluorometer is slightly shifted to a shorter wavelength with respect to that before laser irradiation, and in the circularly polarized luminescence (CPL) measurement, the peak shifts to around 700 nm, that is, shifts to longer wavelength by approximately 200 nm. Thus although by normal fluorescence measurement, only a slight difference was seen in the emission spectra before and after laser irradiation, a difference in circularly polarized luminescence spectrum was detected for the first time by performing the circularly polarized luminescence (CPL) measurement.

Thus by interpreting the circularly polarized luminescence (CPL) peak wavelength shift that occurs due to writing by laser irradiation as 0/1, the circularly polarized light-emitting nanoparticle can be used as a single quantum dot memory. As described above, ferritin has such merits as enabling alignment at a high density due to having a self-aligning ability, shape and size variations of ferritin being extremely low, enabling a low manufacturing cost due to being simple in preparation process, etc., and these merits can be utilized to enable formation of a single quantum dot memory aimed at practical use. Also, the present memory is an optical memory that makes use of circularly polarized luminescence (CPL) and thus a new type of device can be created.

Also, the single quantum dot memory forms a WORM (Write-Once Read-Many times) type single quantum dot memory. That is, with the circularly polarized light-emitting nanoparticle according to the present invention, the circularly polarized luminescence wavelength shifts to longer wavelength due to the compound semiconductor microparticle in the interior undergoing the photooxidation reaction by laser irradiation (the above-described hypothesis), and because this is an irreversible reaction, the emission state is held after the laser irradiation.

Also, by using the wavelength control method for circularly polarized light-emitting nanoparticle, it becomes possible to form a security paint material that contains the circularly polarized light-emitting nanoparticles.

That is, with the paint material that contains the circularly polarized light-emitting nanoparticles according to the present invention, the circularly polarized luminescence wavelength is shifted to longer wavelength by laser irradiation from an exterior, and a security paint material can thus be formed.

Although the circularly polarized luminescence is emitted under excitation light of a predetermined wavelength, the proportion of the right circularly polarized light and the left circularly polarized light cannot be detected visually or by a normal spectrofluorometer, and the paint material having the circularly polarized luminescence property is thus suitable for security applications. As described above, with the circularly polarized light-emitting nanoparticles according to the present invention, the circularly polarized luminescence wavelength can be controlled (shifted) by laser irradiation.

Thus by using the paint material containing the circularly polarized light-emitting nanoparticles according to the present invention, the circularly polarized luminescence wavelength can be changed in a desired portion within a painted area, etc., to enable further fortification of security strength.

Effects of the Invention

By the present invention, a compound semiconductor nanoparticle that exhibits circularly polarized luminescence characteristics can be obtained, and an effect of enabling the compound semiconductor nanoparticle to be aligned and adjusted in size uniformly is provided.

Also, the circularly polarized luminescence wavelength can be adjusted (shifted) by applying laser irradiation or other external stimulus to the compound semiconductor nanoparticle, thereby providing the effect of enabling application to a WORM type single quantum dot memory.

BEST MODE FOR CARRYING OUT THE INVENTION

Embodiments of the present invention will be described in detail below with reference to the drawings.

Example 1

(Preparation Example of Compound Semiconductor Nanoparticles that Exhibit Circularly Polarized Luminescence Characteristics)

First, as an example of a method for preparing compound semiconductor nanoparticles that exhibit circularly polarized luminescence characteristics, a method for forming a microparticle made of cadmium acetate (CdS) inside apoferritin shall be described.

Figure 13:
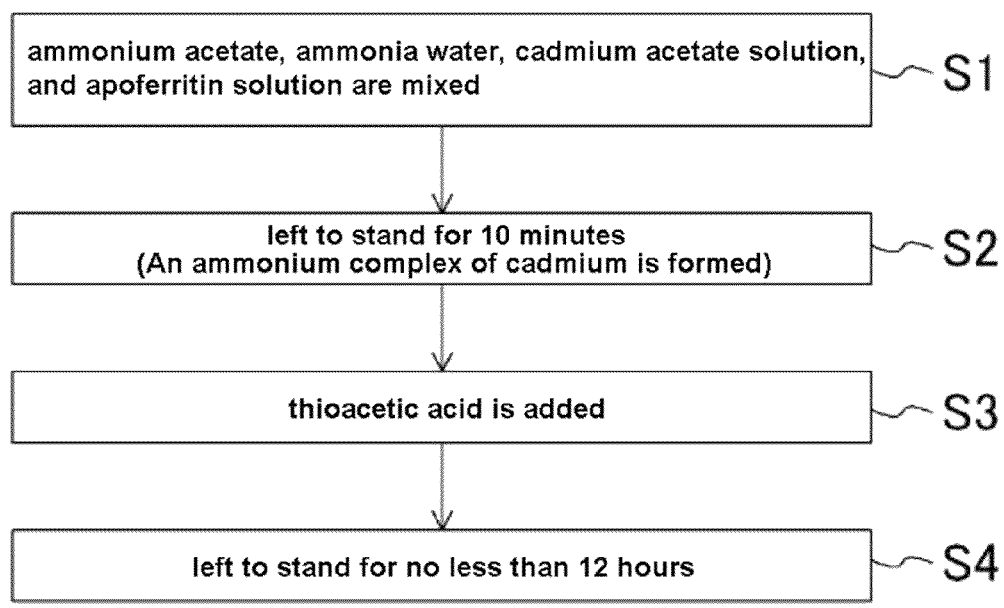
FIG. 13 shows a schematic drawing that shows appearance in which the device for detecting state-change of a wire rod of embodiment 2 is installed in rockbolt.

First, as shown in FIG. 13, an ammonium acetate solution and cadmium acetate are mixed (step S1). Specifically, 1 M ammonium acetate, 1 M ammonia water, and a 100 mM cadmium acetate solution are mixed with 300 mL of pure water. The respective reagents are mixed to prepare a final ammonium acetate concentration of 40 mM, final ammonia concentrations of 7.5 mM, 37.5 mM, and 75 mM, respectively, and a final cadmium acetate concentration of 1 mM. An apoferritin solution is thereafter added to the reaction solution. Specifically, an apoferritin solution of a suitable concentration is added to achieve a final concentration, for example, of 0.3 mg/mL. The concentrations of the respective reagents used in the method of Example 1 are simply examples, and the present invention is not restricted thereto.

Next, the reaction solution prepared in step S1 is left to stand for 10 minutes under room temperature (step S2). An ammonium complex of cadmium is thereby formed.

Next, thioacetic acid ($C_2H_4OS$) is added to the reaction solution (step S3). Specifically, thioacetic acid is added to the reaction solution so that its final concentration is 1 mM. In the present example, horse spleen apoferritin is used as the apoferritin. Also, this apoferritin is made up of the two types of monomer subunits of an L subunit and an H subunit.

Thereafter, the reaction solution is left to stand for no less than 12 hours under room temperature to make a cadmium sulfide (CdS) nanoparticle form inside the apoferritin (step S4). In this process, the pH is made approximately no less than 4.0 and no more than 9.0. The reaction time in the present step S4 may be approximately 24 hours.

Here, examples of concentration ranges of the respective reagents are shown in Table 1 below (the pHs of the respective reagents are 4.0 to 9.0). However, the final concentrations of the respective reagents are not restricted to the values in Table 1 below. Also, it is possible to form the cadmium sulfide (CdS) nanoparticle inside apoferritin even when the final concentration of apoferritin in the reaction solution is outside the range of no less than 0.3 mg/mL and no more than 1 mg/mL. The concentration of ammonium acetate is also not restricted to 40 mM.

TABLE 1

| Reagent name | Final concentration |
| --- | --- |
| Ammonium acetate | 40 mM |
| Ammonia water | 0 mM~100 mM |
| Cadmium acetate solution | 0.2 mM~4 mM |
| Thioacetic acid | 0.2 mM~10 mM |
| Apoferritin solution | 0.3 mg/mL~1.0 mg/mL |

Figure 14:
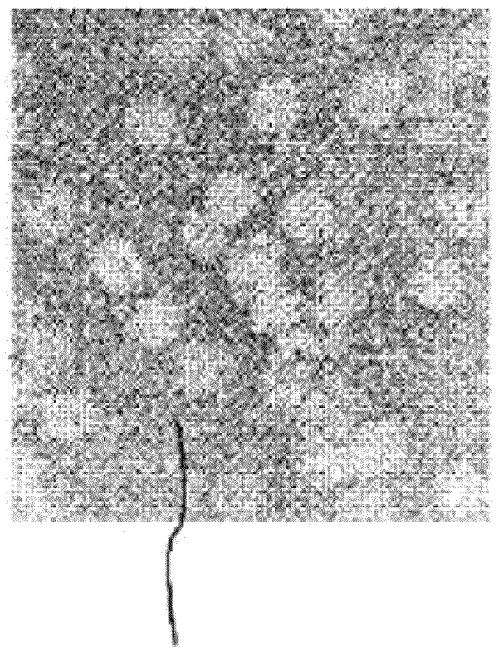
FIG. 14 shows an explanation chart of the device for detecting state-change of a wire rod of embodiment 3.
Figure 14:
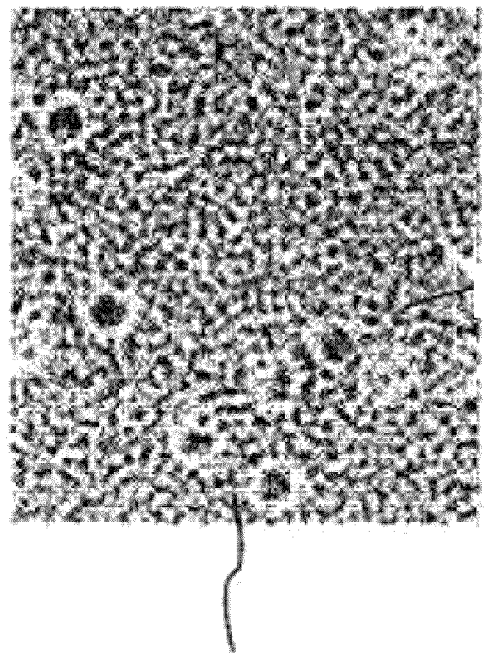

FIG. 14A is a transmission electron microscope (TEM) photograph of apoferritin in the reaction solution in a case where thiourea is used as the sulfur source, and FIG. 14B is a transmission electron microscope (TEM) photograph of apoferritin in the reaction solution in a case where thioacetic acid is used as the sulfur source.

From FIG. 14B, it can be understood that by the method of Example 1, a core (indicated by a black circle in the figure) made up of cadmium sulfides, including CdS, can be formed inside apoferritin. On the other hand, in the case where thiourea is used in place of thioacetic acid as the sulfur source, a core made up of cadmium sulfides was hardly formed in apoferritin.

Figure 15:
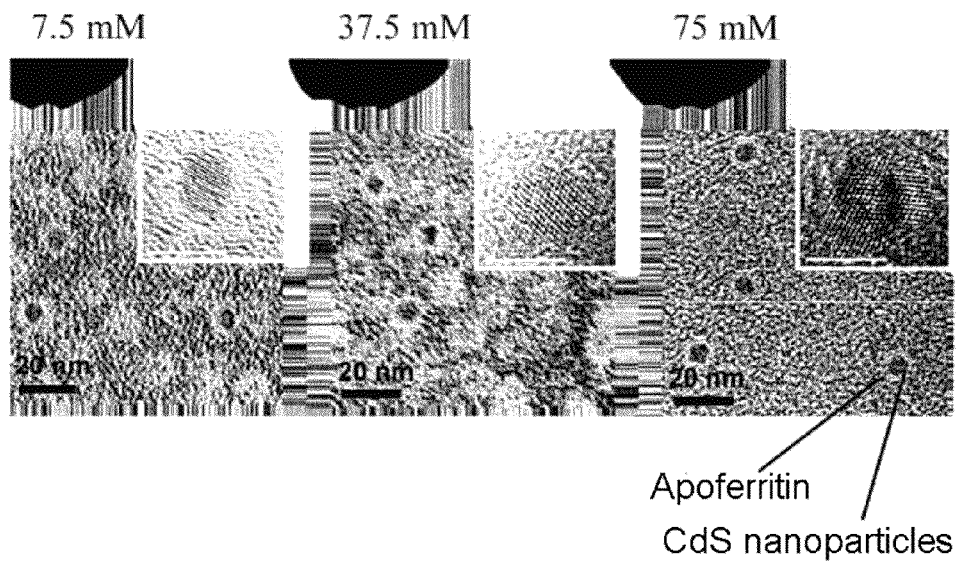
FIG. 15 shows an explanation chart of the device for detecting state-change of a wire rod of embodiment 4.

From the results shown in FIG. 15, it can be understood that cadmium sulfide (CdS) nanoparticles that differ in microparticle diameter were formed inside apoferritin when the ammonia concentration in the reaction solution was varied from 7.5 to 75 mM.

Figure 16:
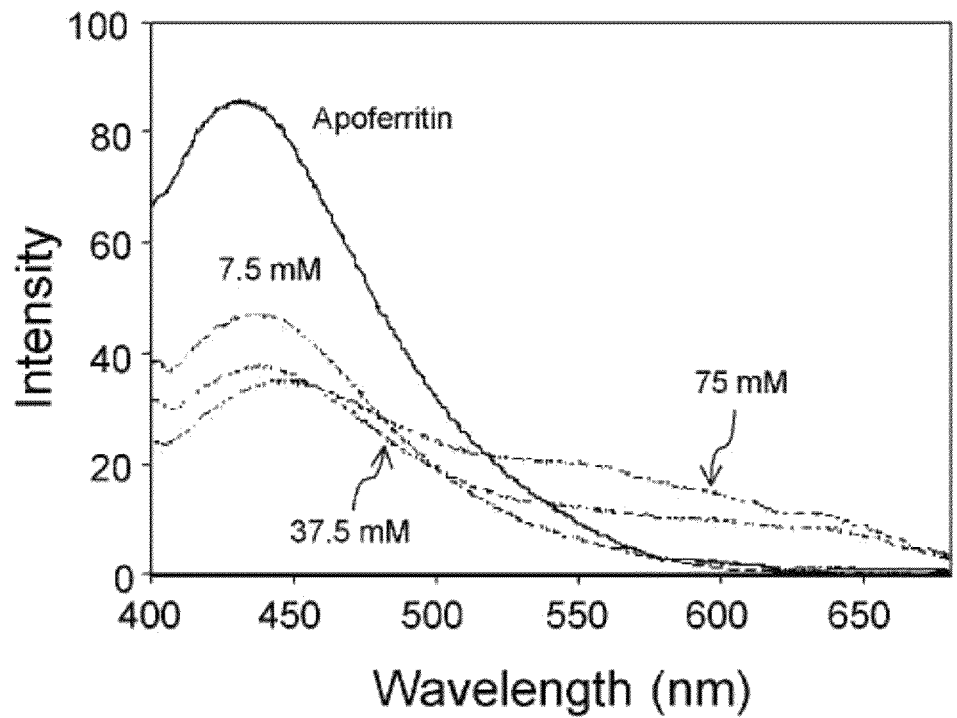
FIG. 16 shows an application example of ferroconcrete.

FIG. 16 is a fluorescence spectrum of the apoferritin having the cadmium sulfide (CdS) nanoparticle formed inside. Here, the fluorescence spectrum for a case where the CdS nanoparticles are excited by light of 350 nm wavelength in the reaction solution containing the apoferritin having the cadmium sulfide (CdS) nanoparticle formed inside is shown. Here, the measurement was made in the reaction solution where the concentration of the apoferritin with the cadmium sulfide (CdS) nanoparticle formed inside was 0.5 mg/mL.

In particular, fluorescence considered to be due to the cadmium sulfide (CdS) nanoparticles was observed near wavelengths of 560 nm, 610 nm, and 640 nm in cases where the ammonia concentration was 37.5 mM and 75 mM. When the reaction solution irradiated with the excitation light was observed visually, the color was blue when the reaction solution contained only apoferritin, and the reaction color changed to a color close to red as the ammonia concentration increased.

Figure 17:
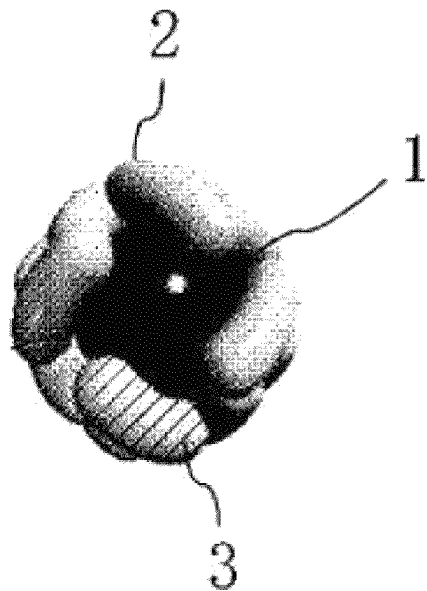
FIG. 17 shows an application example in bedrock discontinuity.

As shown in FIG. 17, the apoferritin with the cadmium sulfide (CdS) nanoparticle formed inside, prepared by the method of Example 1, includes an outer shell 2, made up of a plurality (24) of monomer subunits 3 and having a cavity formed in its interior, and CdS, which is a core microparticle 1, formed in the cavity of the outer shell 2. The CdS that is the core microparticle 1 emits fluorescence when excited.

The apoferritin with the cadmium sulfide (CdS) nanoparticle formed inside can be used in various fields, such as in a semiconductor storage device using microparticles made of CdS as well as in an application as a marker that makes use of the fluorescence emitting characteristic, etc.

Although in step S2 and step S4 shown in FIG. 13, the reaction solution was left to stand under room temperature, it is possible to form the apoferritin with the ammonium complex or the cadmium sulfide (CdS) nanoparticle formed inside under a temperature besides room temperature.

Also, although thioacetic acid is most preferable as the sulfur source, the apoferritin with the cadmium sulfide (CdS) nanoparticle formed inside can also be formed using ammonium sulfide (($NH_4$)$_2$S), a thiosulfate ($K_2S_2O_3$ or $Na_2S_2O_3$), etc., in place of thioacetic acid.

Also, although horse spleen apoferritin was used in the above description, apoferritin derived from another organ (heart, liver, etc.) may be used instead. The cadmium sulfide (CdS) nanoparticle can also be formed inside apoferritin under the same conditions as Example 1 by using an apoferritin from another living organism.

The cadmium sulfide (CdS) nanoparticle can also be formed inside apoferritin using an acetate buffer with ammonia water added or other solution containing ammonium ions and acetate ions in place of the ammonium acetate.

(Characteristics of the Compound Semiconductor Nanoparticles Prepared)

Figure 1:
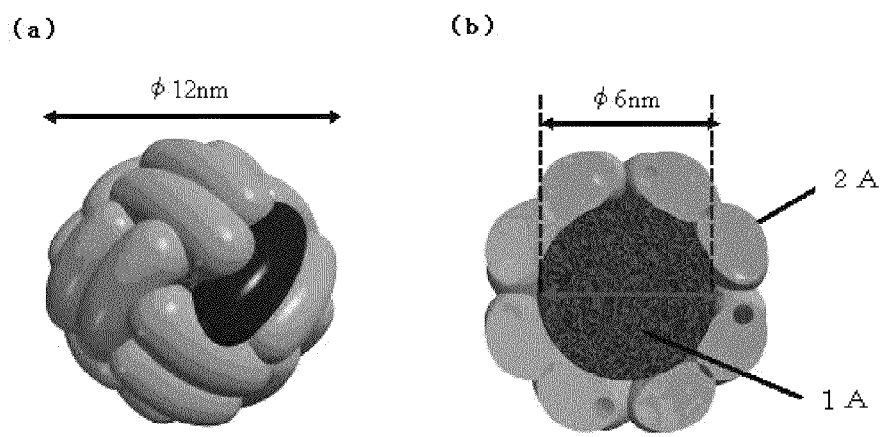
FIG. 1 shows a structural schematic drawing of the device for detecting state-change of a wire rod of embodiment 1.
Figure 2:
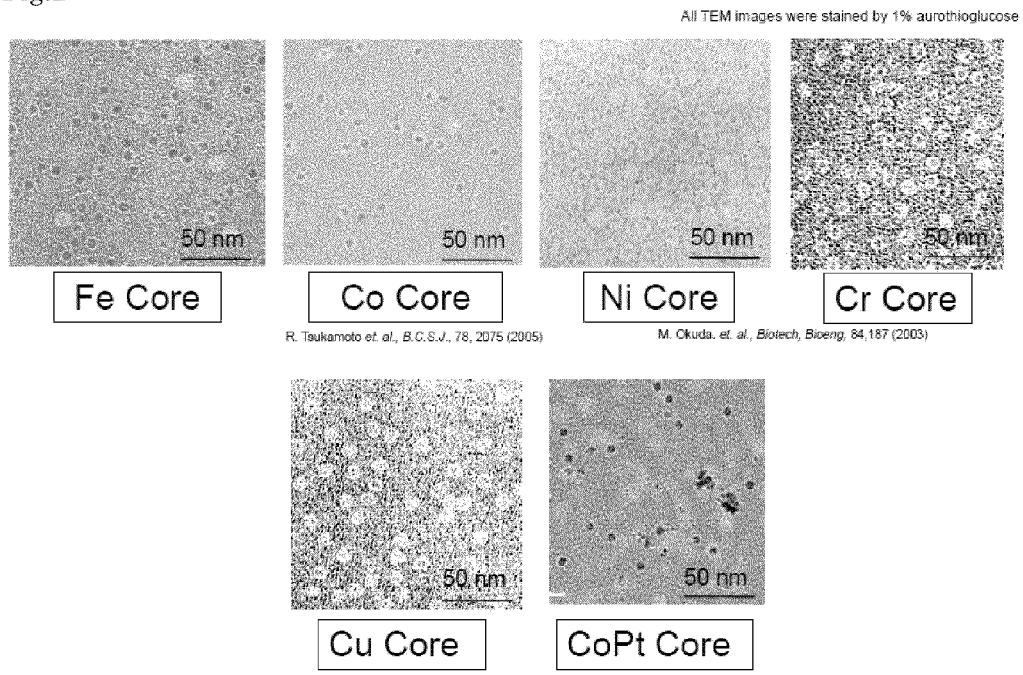
FIG. 2 shows an explanation chart when installing in wire rod (rockbolt) that has exposed one side.
Figure 3:
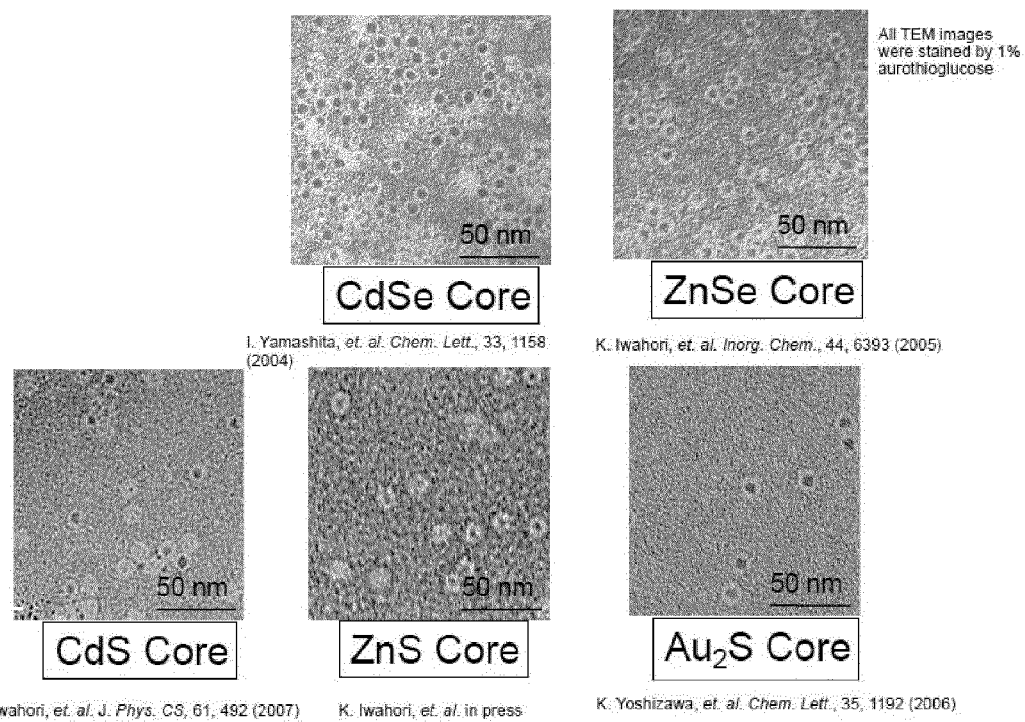
FIG. 3 shows an explanation chart of position of casing of rockbolt.
Figure 4:
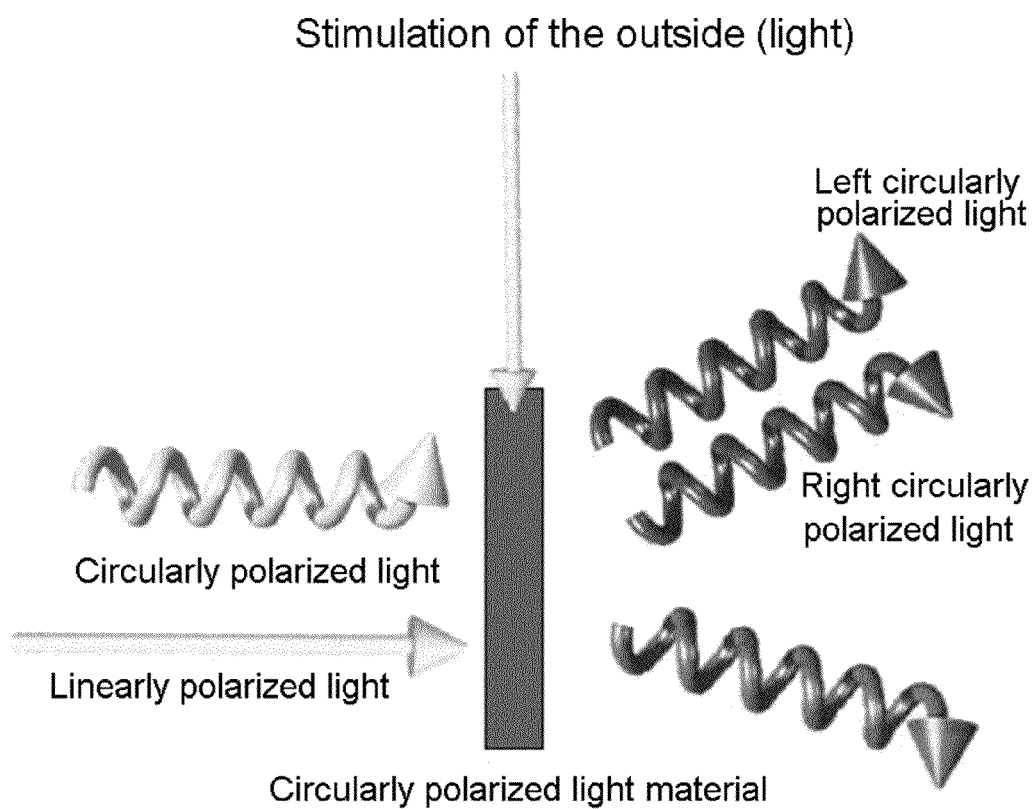
FIG. 4 shows a side view cross section where the device for detecting state-change of a wire rod of embodiment 1 was installed in rockbolt.
Figure 5:
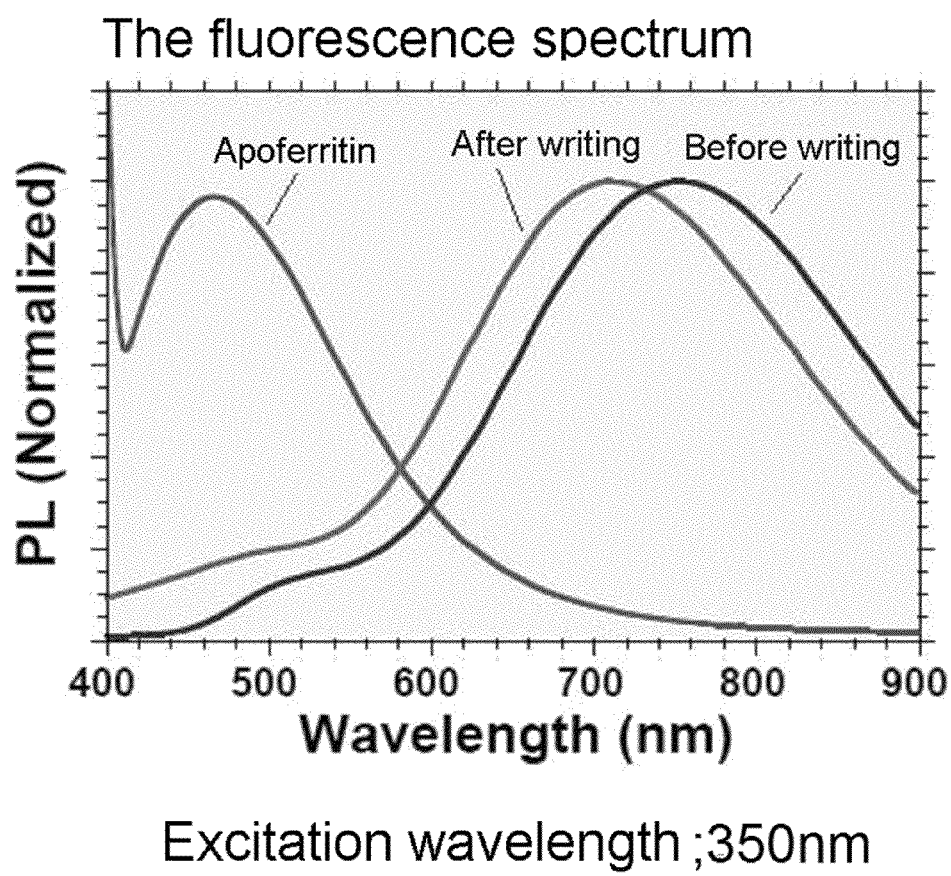
FIG. 5 shows a schematic drawing that shows appearance in which the device for detecting state-change of a wire rod of embodiment 1 is installed in rockbolt.

FIG. 5 shows a fluorescence spectrum of the compound semiconductor nanoparticles prepared as described above. A fluorescence spectrum of apoferritin is also shown for comparison.

It can be confirmed from FIG. 5 that there is a large difference between the fluorescence spectrum of the compound semiconductor nanoparticles and the fluorescence spectrum of apoferritin. It can also be confirmed that by laser irradiation (after writing) of the compound semiconductor nanoparticles prepared, the position of the fluorescence emission wavelength peak is shifted to lower wavelength, that is, shifted from approximately 760 nm to approximately 700 nm. The spectrum of the state before laser irradiation is indicated as "BEFORE WRITING," and the spectrum of the state after laser irradiation is indicated as "AFTER WRITING."

Here, the wavelength of the irradiated laser was 400 nm and the irradiation time was 1 hour. The irradiation time can be controlled by adjusting the laser wavelength.

Figure 6:
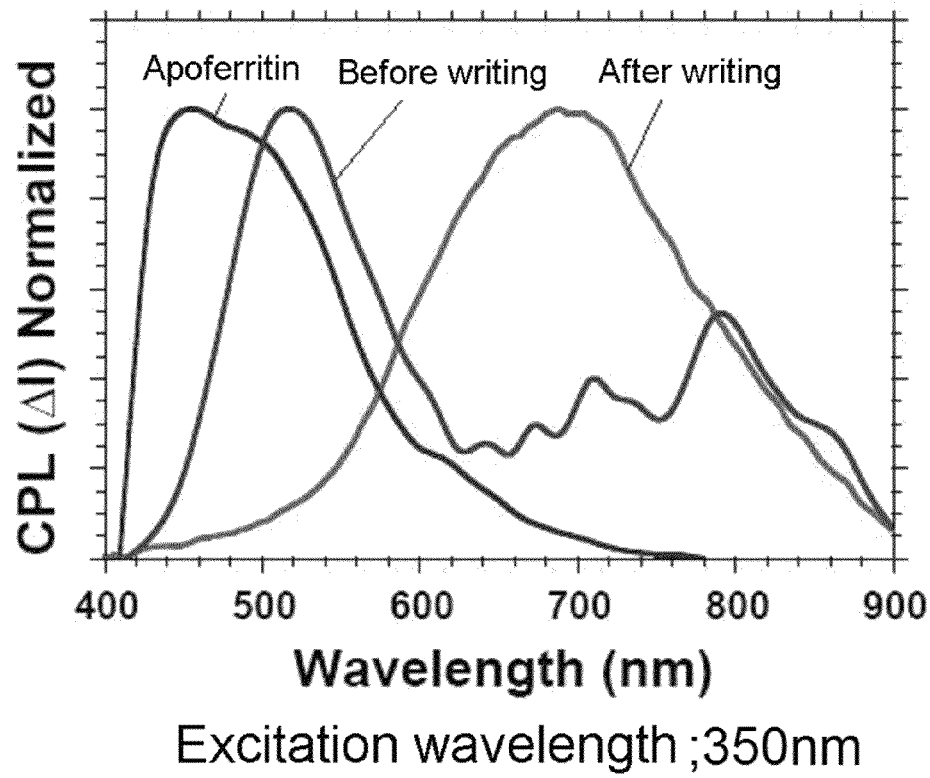
FIG. 6 shows a structural explanation chart of switch unit.

The circularly polarized luminescence characteristics of the compound semiconductor nanoparticles prepared shall now be described with reference to FIG. 6. FIG. 6 shows a circularly polarized luminescence spectrum of the compound semiconductor nanoparticles prepared as described above.

It can be confirmed from FIG. 6 that there is a large difference between the circularly polarized luminescence spectrum of apoferritin and the circularly polarized luminescence spectrum of the compound semiconductor nanoparticles. It can also be confirmed that in comparison to the state before laser irradiation (before writing) of the compound semiconductor nanoparticles prepared, the position of the circularly polarized luminescence peak is shifted to longer wavelength, that is, shifted from approximately 520 nm to approximately 700 nm by the laser irradiation (after writing). The spectrum of the state before laser irradiation is indicated as "BEFORE WRITING," and the spectrum of the state after laser irradiation is indicated as "AFTER WRITING."

A principle of the shift to longer wavelength of the circularly polarized luminescence in the compound semiconductor nanoparticle with which the cadmium sulfide (CdS) nanoparticle is formed inside apoferritin shall now be described with reference to FIG. 7.

Figure 7:
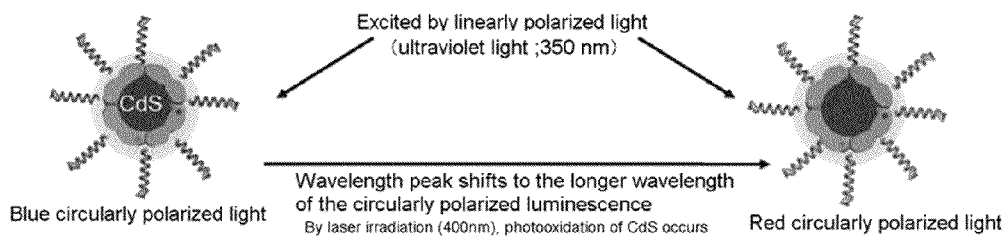
FIG. 7 shows an operation explanation chart of switch unit.

A compound semiconductor nanoparticle with which the cadmium sulfide (CdS) nanoparticle is formed inside apoferritin is shown at a left side of FIG. 7. In the original state (before laser irradiation; before writing), the compound semiconductor nanoparticle has the circularly polarized luminescence wavelength peak at approximately 520 nm as shown in FIG. 6 and thus has a characteristic of emitting a blue circularly polarized light when excited by linearly polarized light (ultraviolet light; 350 nm). By laser irradiation (400 nm) of the compound semiconductor nanoparticle, photooxidation of CdS occurs and the circularly polarized luminescence wavelength peak shifts to the longer wavelength of approximately 700 nm so that a red circularly polarized luminescence characteristic is exhibited as shown at a right side of FIG. 7.

A particle diameter distribution of the CdS nanoparticles in apoferritin before and after laser irradiation shall now be described with reference to FIG. 8 and FIG. 9.

Figure 8:
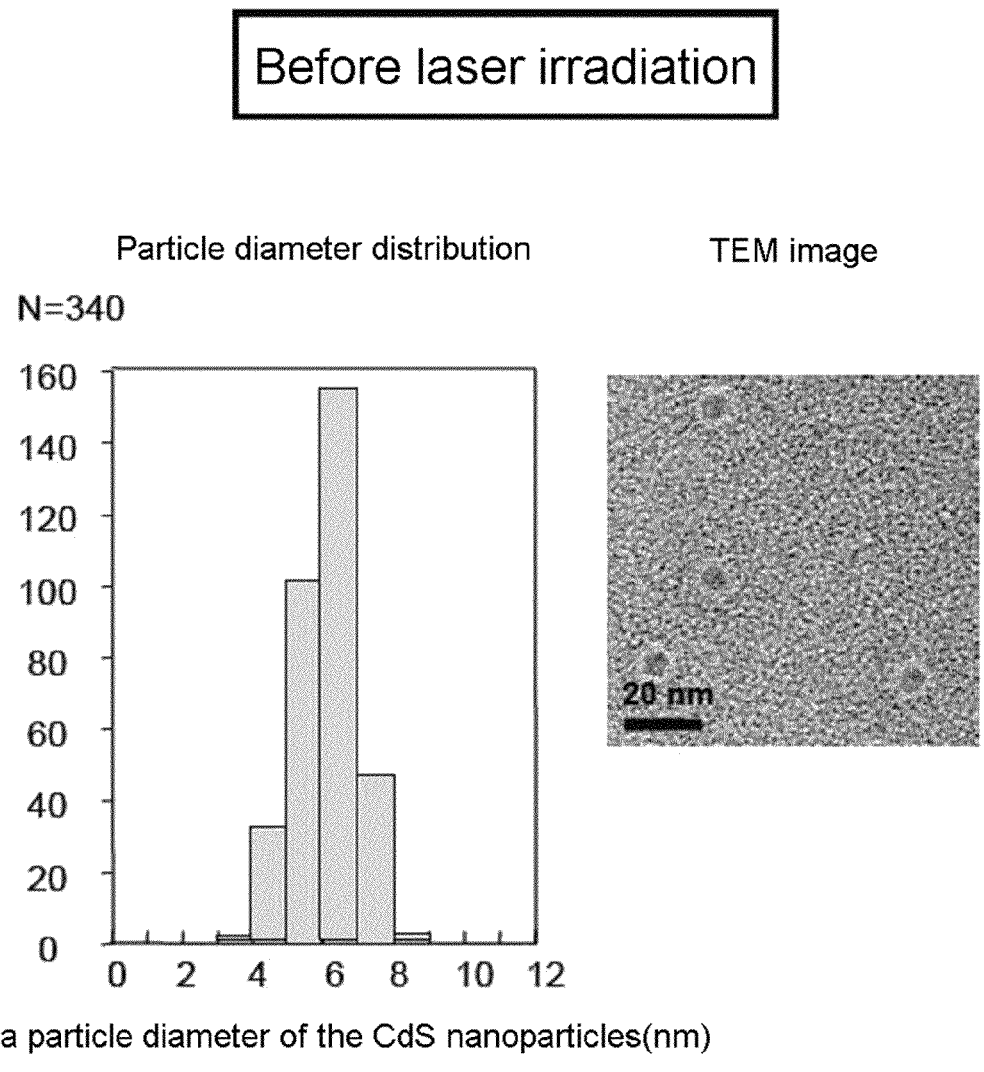
FIG. 8 shows a detailed explanation chart of switch unit.

FIG. 8 shows a particle diameter distribution and a TEM image of the CdS nanoparticles in apoferritin before laser irradiation. Also, FIG. 9 shows a particle diameter distribution and a TEM image of the CdS nanoparticles in apoferritin after laser irradiation.

Figure 9:
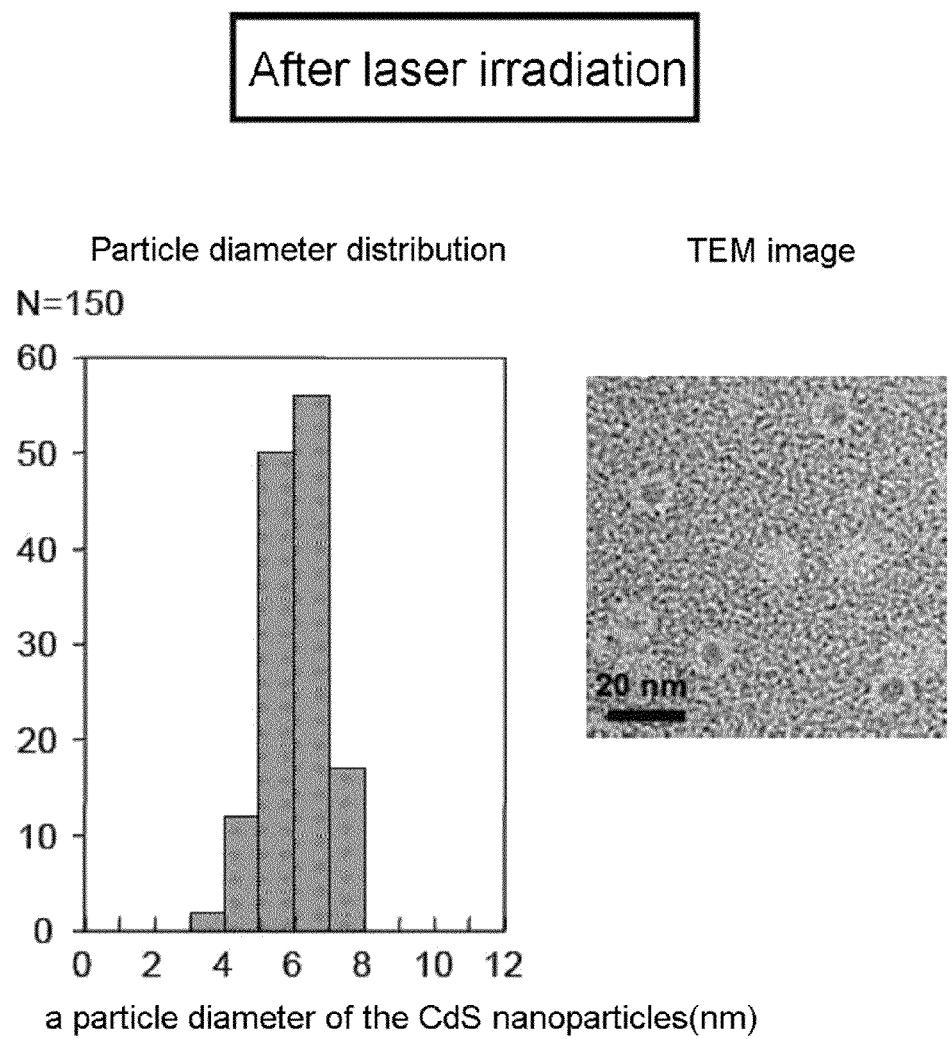
FIG. 9 shows an electric wiring diagram of the device for detecting state-change of a wire rod of embodiment 1.

From FIG. 8 and FIG. 9, it can be understood that whereas before laser irradiation, the particle diameter distribution indicates a diameter of 7.1 nm (variance: 0.7 nm), after laser irradiation, the particle diameter distribution indicates a diameter of 6.2 nm (variance: 0.6 nm) and the diameter size of the nanoparticles is decreased. It is presumed that the decrease in diameter size of the nanoparticles is a cause of the shift to shorter wavelength of the position of the fluorescence emission wavelength peak after laser irradiation (after writing) of the compound semiconductor nanoparticles.

Figure 10:
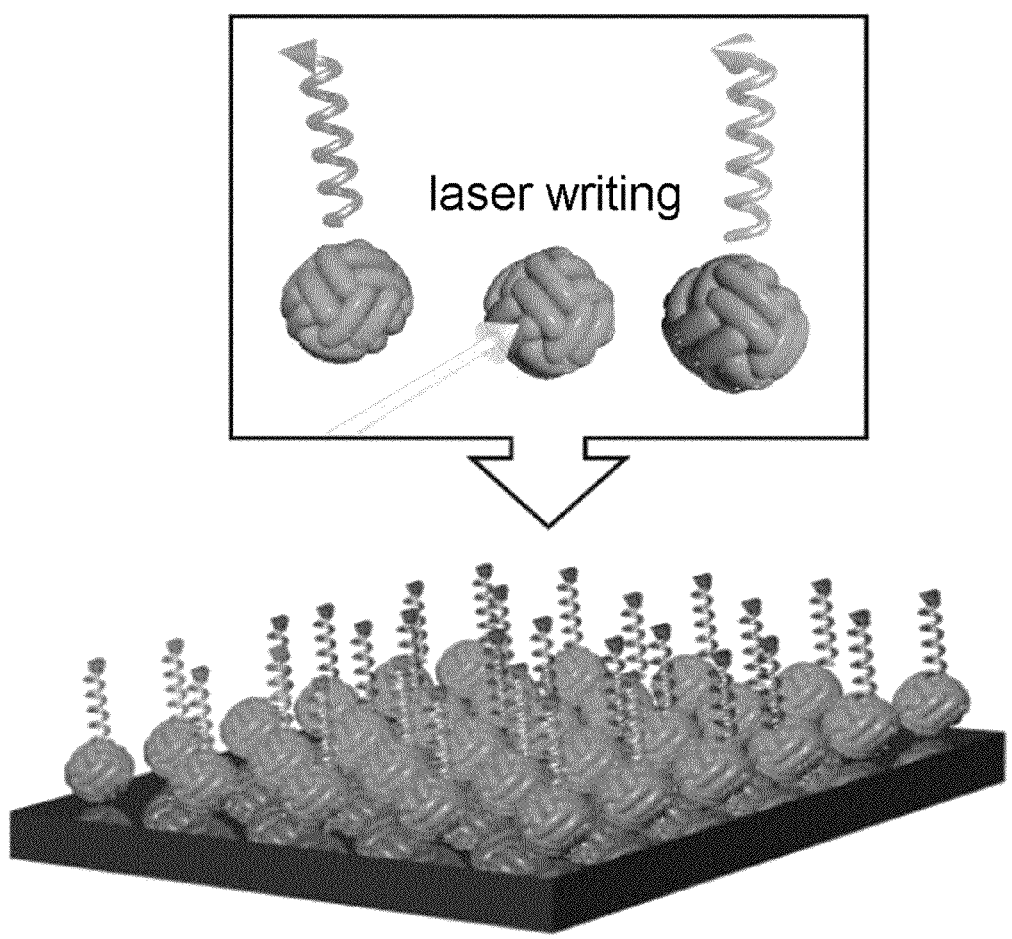
FIG. 10 shows a whole composition chart of the device for detecting state-change of a wire rod of embodiment 1.

A conceptual view of a WORM type single quantum dot memory prepared using the nanoparticles having the above circularly polarized luminescence characteristics and circularly polarized luminescence wavelength shift characteristics is shown in FIG. 10.

As shown in FIG. 10, the prepared nanoparticles are arrayed in two dimensions on a substrate, and by performing laser irradiation (laser writing) on a nanoparticle at a specific position, the circularly polarized luminescence of the nanoparticle is shifted to longer wavelength and the nanoparticle changes from exhibiting a blue circularly polarized luminescence to exhibiting a red circularly polarized luminescence. Use as a storage element for digital information can be realized, for example, by associating the blue circularly polarized luminescence characteristic state with the information bit "1," and associating the red circularly polarized luminescence characteristic state with the information bit "0." Writing can thus be performed not by electrical control but by optical control. Once the blue circularly polarized luminescence characteristic state transits to the red circularly polarized luminescence characteristic state, the original blue circularly polarized luminescence characteristic state cannot be returned to. Creation of a WORM (Write-Once Read-Many times) memory is thus enabled.

Figure 11:
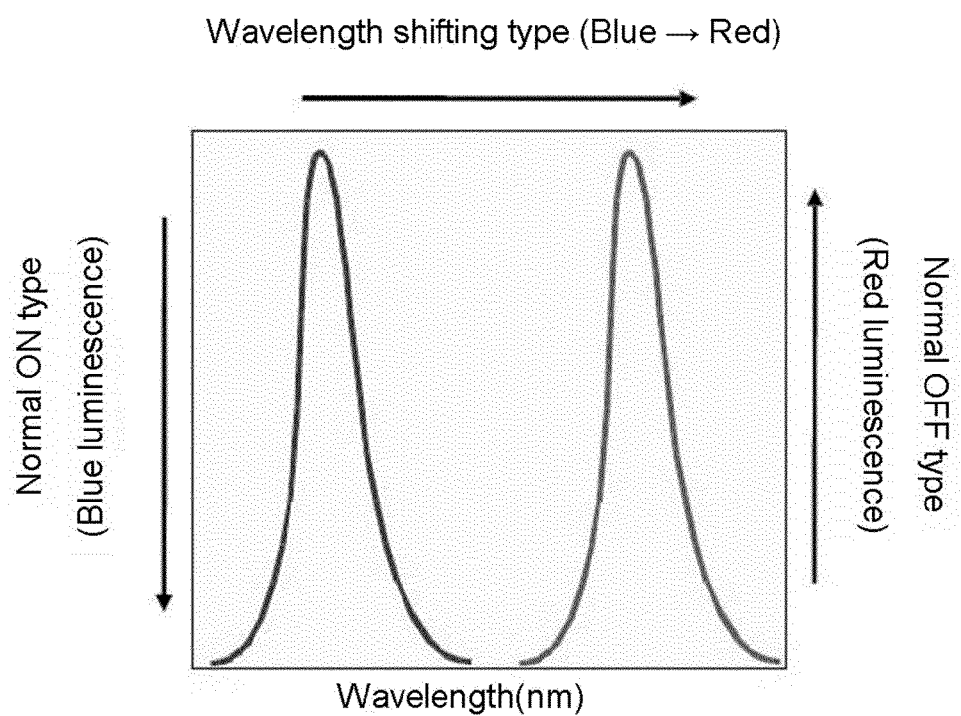
FIG. 11 shows an appearance chart of installation with rockbolt in midair.

Optical reading of the WORM type single quantum dot memory shall now be described with reference to FIG. 11. As shown in FIG. 11, a normal ON type is in the blue luminescence state and a normal OFF type is in the red luminescence state. The single quantum dot formed by an individual nanoparticle is wavelength-shifted by laser irradiation to rewrite the memory information of the single quantum dot. The information can be read by optical measurement of the circularly polarized luminescence of the array of nanoparticles aligned in two dimensions.

The memory according to the present invention can thereby be used as any of the three types of memory of: (1) a memory implementing on/off of blue luminescence; (2) a memory implementing on/off of red luminescence; and (3) a memory implementing wavelength shifting. With all three types, writing can be performed easily by laser irradiation and thus any of these memory types can be suitably selected according to the device to which the memory is to be applied.

Figure 12:
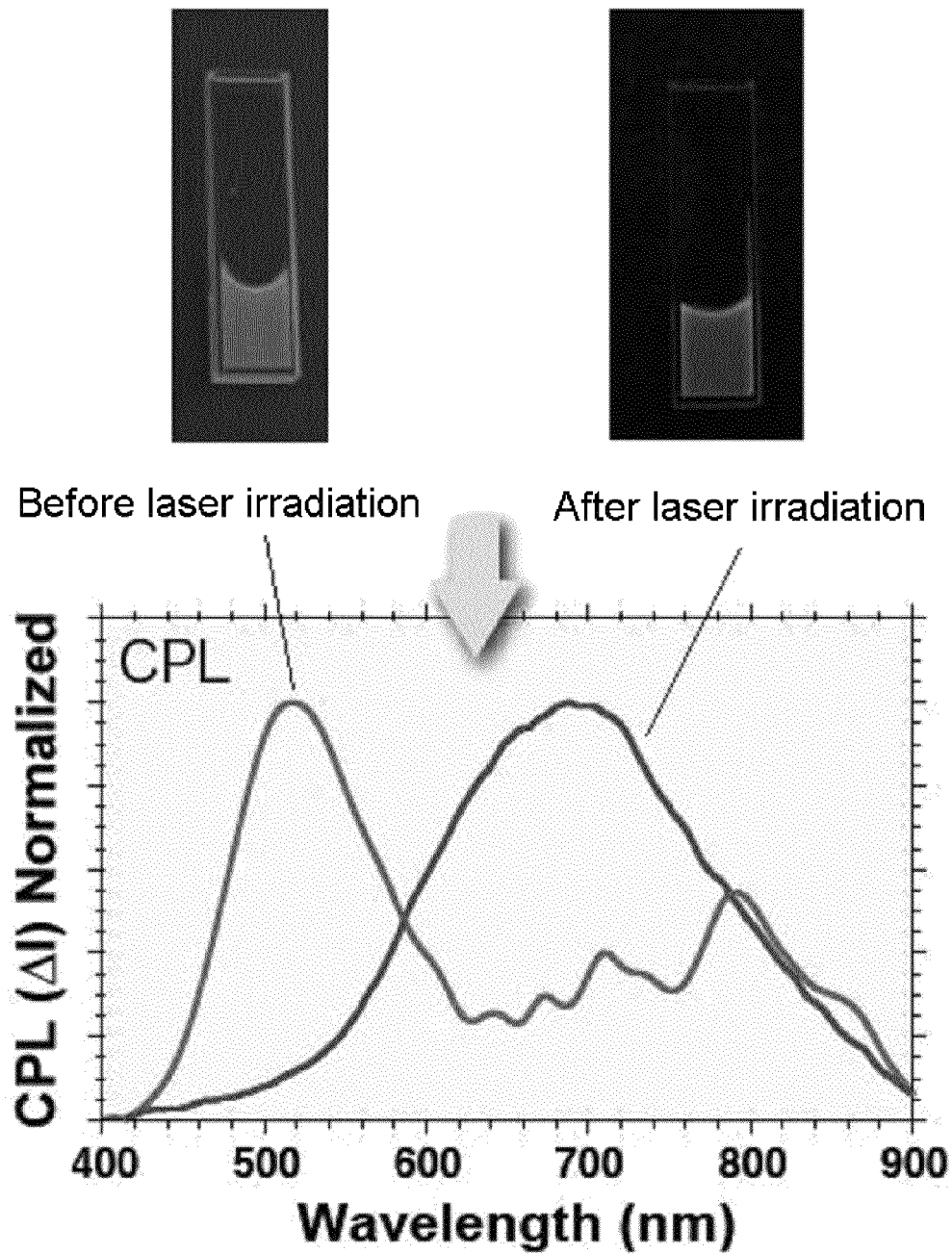
FIG. 12 shows a side view cross section where the device for detecting state-change of a wire rod of embodiment 1 was installed in rockbolt.

As another application of the nanoparticles having the circularly polarized luminescence characteristics and circularly polarized luminescence wavelength shift characteristics, there is the use as a security paint as shown in FIG. 12. Here, utilization as a security paint is realized by making use of the change of circularly polarized luminescence characteristics before and after laser irradiation of a paint material containing the nanoparticles having the circularly polarized luminescence characteristics. The change of information is performed not by electrical control but by optical control as described above and thus employment in a harsh environment or outdoors can be anticipated.

(Preparation Example of Another Type of Compound Semiconductor Nanoparticles that Exhibit Circularly Polarized Luminescence Characteristics)

With Example 1, as an example of a method for preparing compound semiconductor nanoparticles that exhibit circularly polarized luminescence characteristics, the method for forming a microparticle made of cadmium sulfide (CdS) inside apoferritin was described together with the characteristics and applications of the nanoparticles formed.

With Example 2, an example using zinc sulfide (ZnS), which is another compound semiconductor that is a II-VI compound and differs from that of Example 1, shall be described.

First, as an example of a method for preparing compound semiconductor nanoparticles that exhibit circularly polarized luminescence characteristics, a method for forming a microparticle made of zinc sulfide (ZnS) inside apoferritin shall be described.

Figure 18:
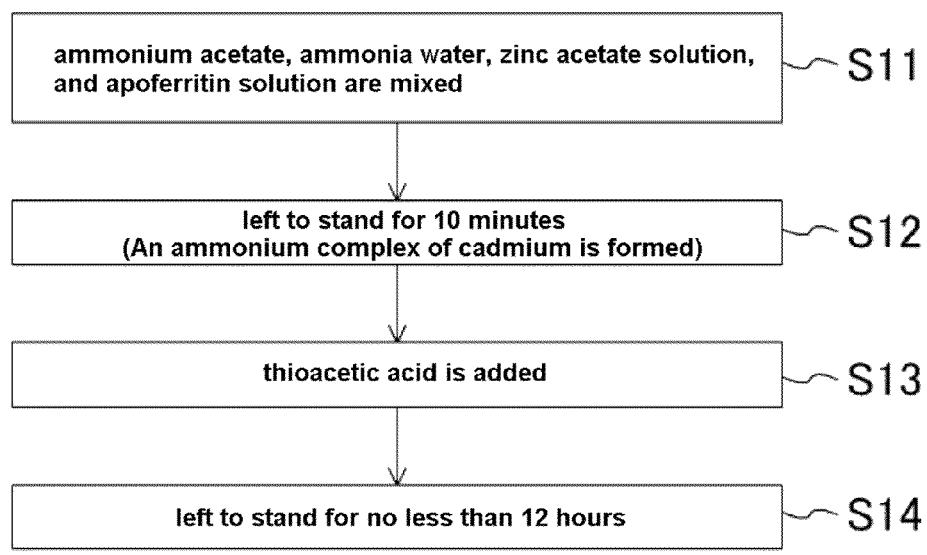
FIG. 18 shows an explanation chart of rigidity cable with part that has taper of embodiment 5.

First, as shown in FIG. 18, an ammonium acetate solution and a zinc acetate solution are mixed (step S11). Specifically, 1 M ammonium acetate, 1 M ammonia water, and a 100 mM zinc acetate solution are mixed with 300 mL of pure water. The respective reagents are mixed to prepare a final ammonium acetate concentration of 40 mM, final ammonia concentrations of 7.5 mM to 75 mM, respectively, and a final zinc acetate concentration of 1 mM. An apoferritin solution is thereafter added to the reaction solution. Specifically, an apoferritin solution of a suitable concentration is added to achieve a final concentration, for example, of 0.3 mg/mL. The concentrations of the respective reagents used in the method of Example 2 are simply examples, and the present invention is not restricted thereto.

Next, the reaction solution prepared in step S11 is left to stand for 10 minutes under room temperature (step S12). An ammonium complex of zinc is thereby formed. Next, thioacetic acid is added to the reaction solution (step S13). Specifically, thioacetic acid is added to the reaction solution so that its final concentration is 10 mM. In the present example, horse spleen apoferritin is used as the apoferritin.

Thereafter, the reaction solution is left to stand for no less than 12 hours under room temperature to make nanoparticles of zinc sulfide form inside apoferritin (step S14). In this process, the pH is made approximately no less than 4.0 and no more than 9.0. Here, the ZnS formed in the apoferritin may, depending on the conditions, be partially ZnS or other zinc 2 sulfide besides ZnS. The reaction time in the present step S14 may be approximately 24 hours.

Here, examples of concentration ranges of the respective reagents are shown in Table 2 below (the pHs of the respective reagents are 4.0 to 9.0). However, the final concentrations of the respective reagents are not restricted to the values in Table 2 below. Also, it is possible to form nanoparticles of zinc sulfide (ZnS) inside apoferritin even when the final concentration of apoferritin in the reaction solution is outside the range of no less than 0.3 mg/mL and no more than 1 mg/mL. The concentration of ammonium acetate is also not restricted to 40 mM.

TABLE 2

| Reagent name | Final concentration |
| --- | --- |
| Ammonium acetate | 40 mM |
| Ammonia water | 0 mM~100 mM |
| Zinc acetate | 0.1 mM~10 mM |
| Thioacetic acid | 0.1 mM~100 mM |
| Apoferritin solution | 0.3 mg/mL~1.0 mg/mL |

Figure 19:
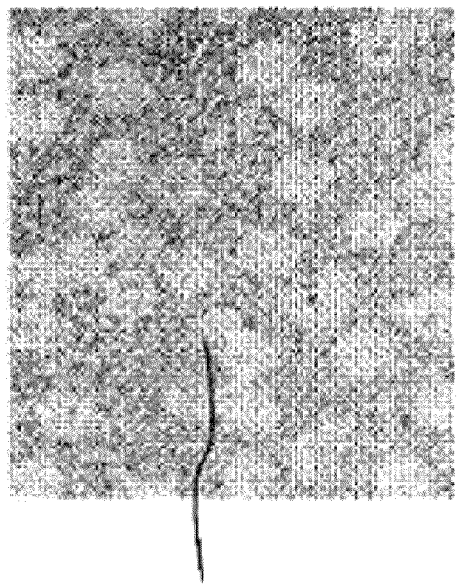
FIG. 19 shows an explanation chart of the first switch unit and the second switch unit composed of elastic member of embodiment 5, and the rigidity cable with part that has taper.
Figure 19:
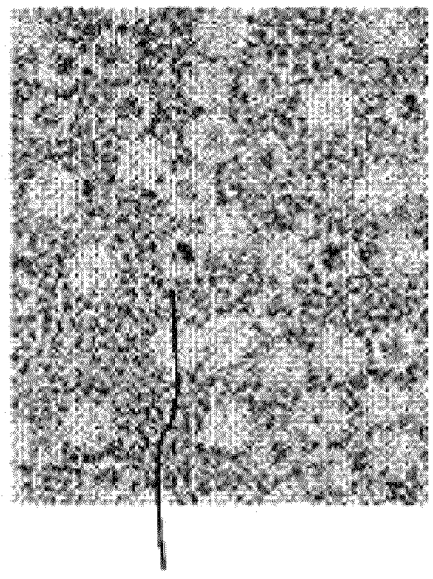

FIG. 19A is a transmission electron microscope (TEM) photograph of apoferritin in the reaction solution in a case where thiourea is used as the sulfur source, and FIG. 19B is a transmission electron microscope (TEM) photograph of apoferritin in the reaction solution in a case where thioacetic acid is used as the sulfur source.

From FIG. 19B, it can be understood that by the method of Example 2, a core made up of zinc sulfides, including ZnS, can be formed inside apoferritin. On the other hand, in the case where thiourea is used in place of thioacetic acid as the sulfur source, a core made up of zinc sulfides was hardly formed inside apoferritin.

Also, although unillustrated, the zinc sulfide (ZnS) nanoparticle could be formed inside apoferritin even when the ammonia concentration in the reaction solution was varied from 0.1 to 100 mM.

Figure 20:
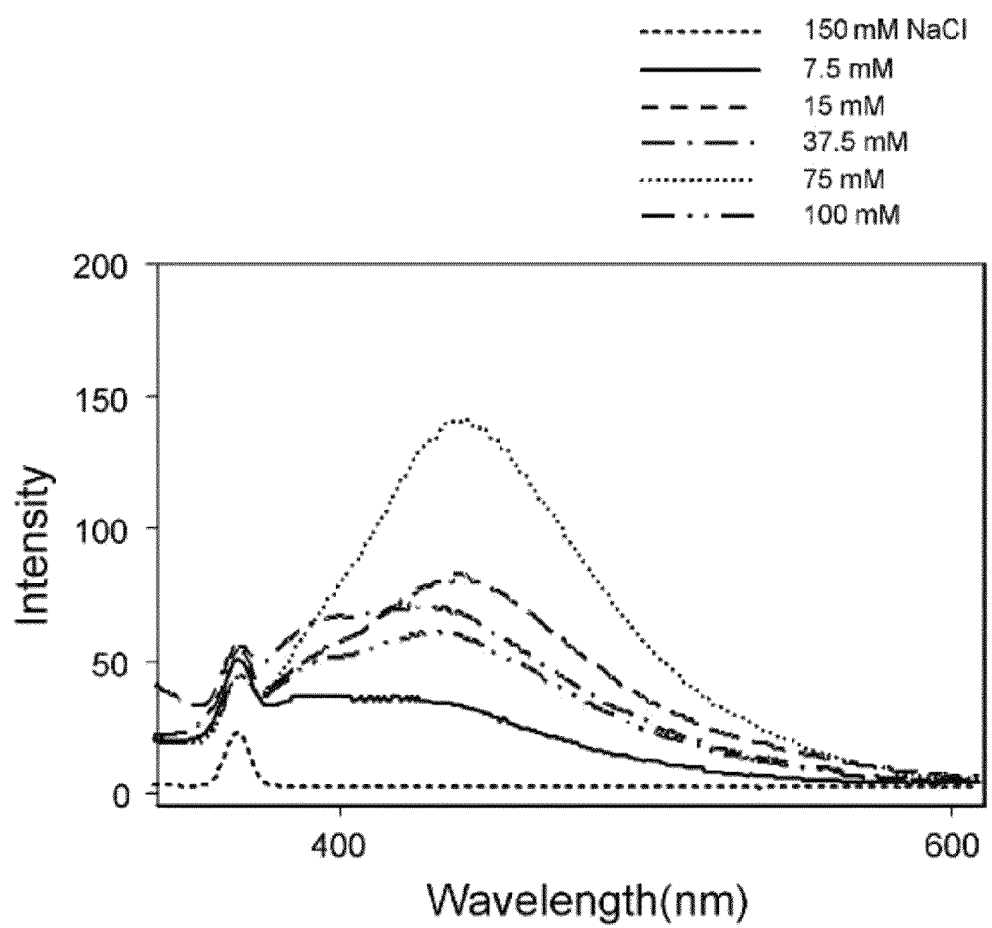
FIG. 20 shows an operation explanation chart of the second switch of embodiment 5. (1) A small transformation was caused. (2) A big transformation was caused.
Figure 21:
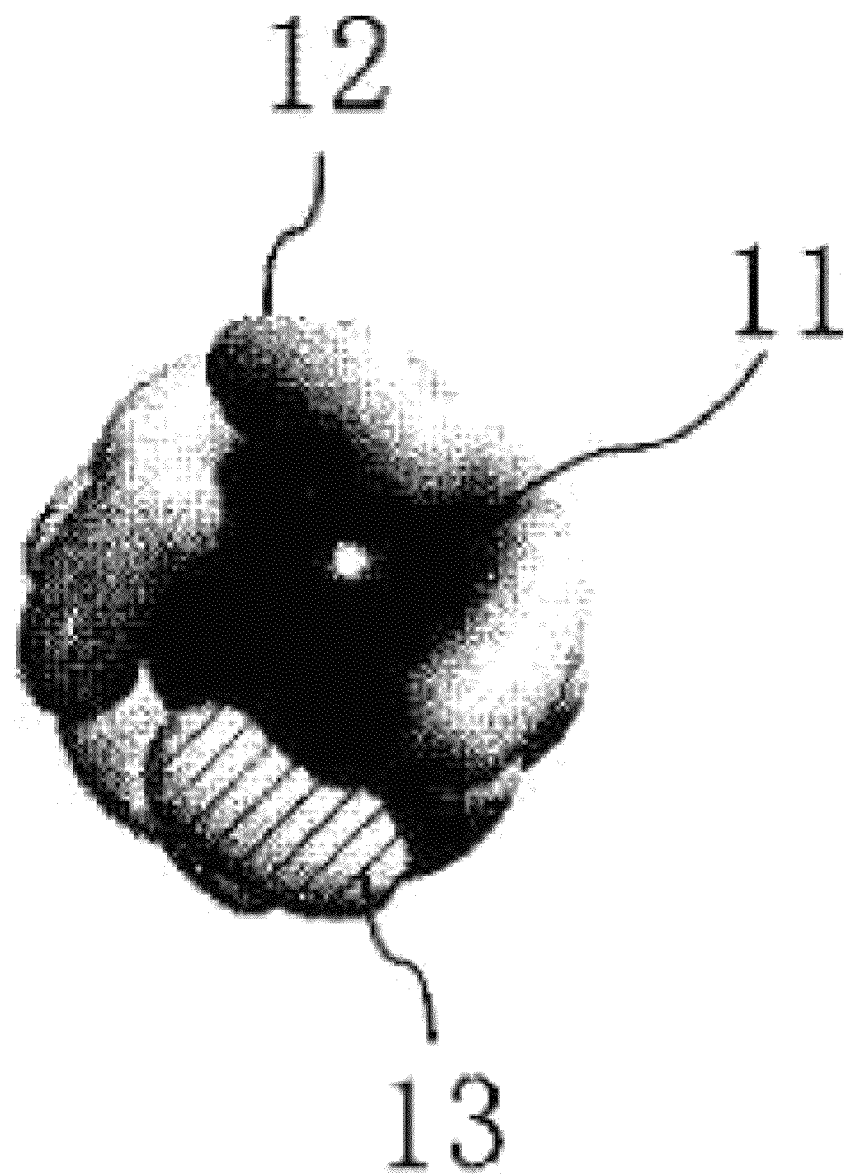
FIG. 21 shows a schematic drawing of device of embodiment 5.

FIG. 20 is a fluorescence spectrum of the apoferritin with the zinc sulfide (ZnS) nanoparticle formed inside. Here, the fluorescence spectrum for a case where the zinc sulfide (ZnS) nanoparticles are excited by light of 325 nm wavelength in the reaction solution containing the nanoparticles with which the ZnS nanoparticle is formed inside apoferritin is shown.

From a comparison with a blank sample, which is a 150 mM NaCl solution, the peak in a region of no more than 400 nm wavelength in FIG. 20 is considered to be due to fluorescence that is not dependent on ZnS particles. Fluorescence considered to be due to the zinc sulfide (ZnS) nanoparticles was observed in a region of 400 to 500 nm wavelength when the ammonia concentration in the reaction solution was in a range of 7.5 mM to 100 mM.

In particular, a stronger fluorescence was observed when the ammonia concentration in the reaction solution was in a range of no less than 15 mM to 100 mM. Visually, the fluorescence due to the ZnS nanoparticles appeared to be blue, and hardly any quenching was observed even after long-term storage (one year). Also, the particle diameter of the ZnS nanoparticles changed with an increase of the ammonia concentration in the reaction solution.

As shown in FIG. 26, the apoferritin with the zinc sulfide (ZnS) nanoparticle formed inside, prepared by the method of Example 2, includes an outer shell 12 made up of a plurality (24) monomer subunits 13 and having a cavity formed in its interior, and a core (microparticle) 11, which is made of ZnS formed inside the cavity of the outer shell 12 and emits fluorescence when excited.

The apoferritin with the zinc sulfide (ZnS) nanoparticle formed inside apoferritin according to Example 2 can be used in various fields, such as in a semiconductor storage device using microparticles made of ZnS, in an application as a marker that makes use of the fluorescence emitting characteristic, etc.

Although in step S12 and step S14 shown in FIG. 18, the reaction solution was left to stand under room temperature, it is possible to form the apoferritin with the ammonium complex or the zinc sulfide (ZnS) nanoparticle formed inside even under a temperature besides room temperature.

Also, although thioacetic acid is most preferable as the sulfur source, the apoferritin with the zinc sulfide (ZnS) nanoparticle formed inside can also be formed using ammonium sulfide (($NH_4$)$_2$S), a thiosulfate ($K_2S_2O_3$ or $Na_2S_2O_3$), etc., in place of thioacetic acid.

Also, although horse spleen apoferritin was used in the above description, an apoferritin derived from another organ (heart, liver, etc.) may be used instead. The zinc sulfide (ZnS) nanoparticle can also be formed inside apoferritin under the same conditions as Example 2 by using an apoferritin from another living organism.

The zinc sulfide (ZnS) nanoparticle can also be formed inside apoferritin using an acetate buffer with ammonia water added or other solution containing ammonium ions and acetate ions in place of the ammonium acetate.

INDUSTRIAL APPLICABILITY

The circularly polarized light-emitting microparticle according to the present invention can be used in a WORM memory, a security paint, or a verification system having these as components.

DESCRIPTION OF SYMBOLS 1A core portion
2A protein outer shell portion
1, 11 core
2, 12 outer shell
3, 13 monomer subunit

The invention claimed is:
1. A circularly polarized light-emitting nanoparticle comprising a compound semiconductor nanoparticle encapsu- lated in a protein cage, further characterized in that a circularly polarized luminescence wavelength is controlled by laser irradiation of the nanoparticle.

2. The circularly polarized light-emitting nanoparticle according to claim 1, wherein the protein is apoferritin.

3. The circularly polarized light-emitting nanoparticle according to claim 1, wherein the compound semiconductor is a II-VI compound semiconductor.

4. The circularly polarized light-emitting nanoparticle according to claim 3, wherein the II-VI compound semiconductor is CdS or ZnS.

5. A quantum dot memory, wherein circularly polarized light-emitting nanoparticles according to claim 1 are disposed two-dimensionally inside an insulating film layer.

6. A WORM type single quantum dot memory comprising circularly polarized light-emitting nanoparticles according to claim 1.

7. A security paint material comprising circularly polarized light-emitting nanoparticles according to claim 1.

8. A circularly polarized light-emitting nanoparticle comprising a compound semiconductor nanoparticle that is surface-modified by a protein, further characterized in that a circularly polarized luminescence wavelength is controlled by laser irradiation of the nanoparticle.

9. The circularly polarized light-emitting nanoparticle according to claim 8, wherein the compound semiconductor is a II-VI compound semiconductor or a III-V compound semiconductor.

10. A wavelength control method comprising obtaining a compound semiconductor nanoparticle encapsulated in a protein cage, and controlling a circularly polarized luminescence wavelength by laser irradiation of the circularly polarized light-emitting nanoparticle.

11. The wavelength control method according to claim 10, wherein the circularly polarized luminescence wavelength is shifted to a longer wavelength by the laser irradiation.

12. The wavelength control method according to claim 10, wherein an emission wavelength is shifted to a shorter wavelength by the laser irradiation.

* * * * *